US011497638B2

(12) United States Patent
Pedroso et al.

(10) Patent No.: US 11,497,638 B2
(45) Date of Patent: Nov. 15, 2022

(54) SYSTEMS AND METHODS OF MANUFACTURING AND USING AN EXPANSION RING

(71) Applicant: DePuy Synthes Products, Inc., Raynham, MA (US)

(72) Inventors: Pedro Pedroso, Raynham, MA (US); Christopher Krier, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/399,219

(22) Filed: Aug. 11, 2021

(65) Prior Publication Data

US 2021/0369476 A1 Dec. 2, 2021

Related U.S. Application Data

(62) Division of application No. 16/845,589, filed on Apr. 10, 2020, now Pat. No. 11,090,175, which is a
(Continued)

(51) Int. Cl.
*A61F 2/90* (2013.01)
*A61F 2/07* (2013.01)
(Continued)

(52) U.S. Cl.
CPC ............... *A61F 2/90* (2013.01); *A61F 2/07* (2013.01); *A61F 2/848* (2013.01); *A61F 2/92* (2013.01);
(Continued)

(58) Field of Classification Search
CPC ......... A61F 2/90; A61F 2240/001; A61F 2/07
See application file for complete search history.

(56) References Cited

U.S. PATENT DOCUMENTS 4,332,278 A 4/1982 Lalikos
4,610,688 A 9/1986 Silvestrini
(Continued)

FOREIGN PATENT DOCUMENTS

CN 101234046 A 8/2008
CN 101779992 A 7/2010
(Continued)

OTHER PUBLICATIONS

Ansaar T. Rai et al., "Cerebrovascular geometry in the anterior circulation: an analysis of diameter, length and the vessel taper", J NeuroIntervent Surg 2013; 5: 371-375_doi: 10_1136/neurintsurg-2012-010314; Apr. 4, 2012.
(Continued)

*Primary Examiner* — Moshe Wilensky
*Assistant Examiner* — Michael W Hotchkiss
(74) *Attorney, Agent, or Firm* — Troutman Pepper Hamilton Sanders LLP

(57) ABSTRACT

A method of connecting an expansion ring to at least one end of a braided implant, the method including positioning the braided implant about a tube; everting an end portion of the braided implant over a first end of the tube; assembling an expansion ring to the braided implant, the expansion ring being a multi-leaved expansion ring comprising clips terminating with an open-ended coupling opening, wherein the openings are pushed over a set of intersecting wires of the braided implant at respective circumferential locations on or adjacent the first end of the tube; closing the openings over the set of intersecting wire; trimming ends of the braided implant; and reversing eversion of the braided implant thereby positioning the expansion ring internal to the braided implant.

15 Claims, 11 Drawing Sheets

Related U.S. Application Data division of application No. 16/526,749, filed on Jul. 30, 2019, now Pat. No. 10,646,361.

(60) Provisional application No. 62/711,775, filed on Jul. 30, 2018.

(51) Int. Cl.
*A61F 2/92* (2013.01)
*A61F 2/848* (2013.01)
*A61F 2/82* (2013.01)
*A61F 2/966* (2013.01)
*A61F 2/844* (2013.01)

(52) U.S. Cl.
CPC ......... *A61F 2/844* (2013.01); *A61F 2002/823* (2013.01); *A61F 2002/9665* (2013.01); *A61F 2250/0098* (2013.01)

(56) References Cited

U.S. PATENT DOCUMENTS

| | | | |
|---|---|---|---|
| 4,754,685 A | 7/1988 | Kite | |
| 5,064,435 A | 11/1991 | Porter | |
| 5,275,622 A | 1/1994 | Lazarus et al. | |
| 5,282,824 A | 2/1994 | Gianturco | |
| 5,330,500 A | 7/1994 | Song | |
| 5,382,259 A | 1/1995 | Phelps et al. | |
| 5,387,235 A | 2/1995 | Chuter | |
| 5,423,849 A | 6/1995 | Engelson | |
| 5,476,508 A | 12/1995 | Amstrup | |
| 5,522,881 A | 6/1996 | Lentz | |
| 5,549,662 A | 8/1996 | Fordenbacher | |
| 5,556,413 A | 9/1996 | Lam | |
| 5,601,593 A | 2/1997 | Freitag | |
| 5,609,627 A | 3/1997 | Goicoechea | |
| 5,645,558 A | 7/1997 | Horton | |
| 5,662,622 A | 9/1997 | Gore | |
| 5,702,418 A | 12/1997 | Ravenscroft | |
| 5,725,549 A | 3/1998 | Lam | |
| 5,728,131 A | 3/1998 | Frantzen | |
| 5,755,772 A | 5/1998 | Evans et al. | |
| 5,769,887 A | 6/1998 | Brown | |
| 5,776,161 A | 7/1998 | Globerman | |
| 5,817,126 A | 10/1998 | Imran | |
| 5,849,037 A | 12/1998 | Frid | |
| 5,851,217 A | 12/1998 | Wolff | |
| 5,855,601 A * | 1/1999 | Bessler | A61F 2/2418 623/2.38 |
| 5,899,935 A | 5/1999 | Ding | |
| 5,916,235 A | 6/1999 | Guglielmi | |
| 5,916,264 A | 6/1999 | Von Oepen | |
| 5,961,546 A | 10/1999 | Robinson et al. | |
| 6,010,529 A | 1/2000 | Herweck | |
| 6,015,432 A | 1/2000 | Rakos et al. | |
| 6,033,436 A | 3/2000 | Steinke | |
| 6,036,725 A | 3/2000 | Avellanet | |
| 6,051,020 A | 4/2000 | Goicoechea | |
| 6,099,559 A | 8/2000 | Nolting | |
| 6,110,198 A | 8/2000 | Fogarty | |
| 6,123,722 A | 9/2000 | Fogarty et al. | |
| 6,123,723 A | 9/2000 | Konya et al. | |
| 6,152,956 A | 11/2000 | Pierce | |
| 6,161,399 A | 12/2000 | Jayaraman | |
| 6,165,213 A | 12/2000 | Goicoechea | |
| 6,168,621 B1 | 1/2001 | Vrba | |
| 6,176,875 B1 | 1/2001 | Lenker | |
| 6,264,683 B1 | 7/2001 | Stack et al. | |
| 6,280,465 B1 | 8/2001 | Cryer | |
| 6,319,278 B1 | 11/2001 | Quinn | |
| 6,325,823 B1 | 12/2001 | Horzewski | |
| 6,348,066 B1 | 2/2002 | Pinchuk et al. | |
| 6,391,037 B1 | 5/2002 | Greenhalgh | |
| 6,409,755 B1 | 6/2002 | Vrba | |
| 6,488,702 B1 | 12/2002 | Besselink | |
| 6,612,012 B2 | 9/2003 | Mitelberg et al. | |
| 6,626,936 B2 | 9/2003 | Stinson | |
| 6,635,080 B1 | 10/2003 | Lauterjung et al. | |
| 6,673,106 B2 | 1/2004 | Mitelberg | |
| 6,699,277 B1 | 3/2004 | Freidberg et al. | |
| 6,740,113 B2 | 5/2004 | Vrba | |
| 6,673,107 B1 | 6/2004 | Brandt | |
| 6,770,089 B1 | 8/2004 | Hong et al. | |
| 6,818,013 B2 | 11/2004 | Mitelberg | |
| 6,833,003 B2 | 12/2004 | Jones | |
| 6,899,914 B2 | 5/2005 | Schmitz | |
| 6,911,040 B2 | 6/2005 | Johnson et al. | |
| 6,918,928 B2 | 7/2005 | Wolinsky | |
| 6,929,659 B2 | 8/2005 | Pinchuk | |
| 6,945,994 B2 | 9/2005 | Austin et al. | |
| 6,955,685 B2 | 10/2005 | Escamilla | |
| 6,960,227 B2 | 11/2005 | Jones | |
| 6,960,228 B2 | 11/2005 | Mitelberg et al. | |
| 6,970,734 B2 | 11/2005 | Eidenschink | |
| 7,001,422 B2 | 2/2006 | Escamilla | |
| 7,037,331 B2 | 5/2006 | Mitelberg | |
| 7,122,052 B2 | 10/2006 | Greenhaigh | |
| 7,153,324 B2 * | 12/2006 | Case | A61F 2/2412 623/1.11 |
| 7,201,769 B2 | 4/2007 | Jones et al. | |
| 7,208,008 B2 | 4/2007 | Clarke | |
| 7,267,685 B2 | 9/2007 | Butaric | |
| 7,288,111 B1 | 10/2007 | Holloway et al. | |
| 7,291,167 B2 | 11/2007 | DiCaprio | |
| 7,309,351 B2 | 12/2007 | Escamilla et al. | |
| 7,344,559 B2 | 3/2008 | Gray | |
| 7,462,190 B2 | 12/2008 | Lombardi | |
| 7,480,973 B2 | 1/2009 | Miller | |
| 7,628,806 B2 | 12/2009 | Yampolsky et al. | |
| 7,632,302 B2 | 12/2009 | Vreeman et al. | |
| 7,641,647 B2 | 1/2010 | Gunderson | |
| 7,655,031 B2 | 2/2010 | Tenne et al. | |
| 7,655,034 B2 | 2/2010 | Mitchell et al. | |
| 7,708,773 B2 | 5/2010 | Pinchuk et al. | |
| 7,758,629 B2 | 7/2010 | Holloway et al. | |
| 7,761,138 B2 | 7/2010 | Wang | |
| 7,806,919 B2 | 10/2010 | Bloom et al. | |
| 7,806,923 B2 | 10/2010 | Moloney | |
| RE42,244 E | 3/2011 | Boatman | |
| 7,913,371 B2 | 3/2011 | Klocke | |
| 7,985,213 B2 | 7/2011 | Parker | |
| 7,998,187 B2 | 8/2011 | Hartley et al. | |
| 8,021,418 B2 | 9/2011 | Gerberding | |
| 8,043,353 B2 | 10/2011 | Kaufmann et al. | |
| 8,043,357 B2 | 10/2011 | Hartley | |
| 8,048,139 B2 | 11/2011 | Frid et al. | |
| 8,052,741 B2 * | 11/2011 | Bruszewski | D04C 1/06 623/1.35 |
| 8,092,510 B2 | 1/2012 | Metcalf et al. | |
| 8,142,456 B2 | 3/2012 | Rosqueta | |
| 8,152,833 B2 | 4/2012 | Zaver | |
| 8,182,523 B2 | 5/2012 | Tenne et al. | |
| 8,187,316 B2 | 5/2012 | Kuppurathanam | |
| 8,357,194 B2 | 1/2013 | Majercak | |
| 8,372,133 B2 | 2/2013 | Douk et al. | |
| 8,394,119 B2 | 3/2013 | Zaver | |
| 8,449,600 B2 | 5/2013 | Hartley et al. | |
| 8,449,604 B2 | 5/2013 | Moaddeb | |
| 8,484,120 B2 | 7/2013 | Hagaman et al. | |
| 8,562,666 B2 | 10/2013 | Bonsignore | |
| 8,579,959 B2 | 11/2013 | Ducke | |
| 8,597,276 B2 | 12/2013 | Vongphakdy et al. | |
| 8,636,791 B1 | 1/2014 | Raju et al. | |
| 8,641,748 B2 | 2/2014 | Hebert et al. | |
| 8,672,992 B2 | 3/2014 | Orr | |
| 8,709,065 B2 | 4/2014 | Chobotov | |
| 8,734,501 B2 | 5/2014 | Hartley et al. | |
| 8,778,008 B2 | 7/2014 | Amplatz et al. | |
| 8,816,247 B1 | 8/2014 | Janardhan et al. | |
| 8,864,811 B2 | 10/2014 | Kao | |
| 9,078,731 B2 | 7/2015 | Mortarino | |
| 9,192,462 B2 * | 11/2015 | Vinluan | A61F 2/958 |
| 9,232,992 B2 | 1/2016 | Heidner | |
| 9,301,864 B2 | 4/2016 | Kao | |

(56) References Cited

U.S. PATENT DOCUMENTS

| | | |
|---|---|---|
| 9,320,590 B2 | 4/2016 | Zaver |
| 9,339,260 B2 | 5/2016 | Eidenschink et al. |
| 9,427,343 B2 | 8/2016 | Bogert |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Bumes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,004,513 B2 * | 6/2018 | Leopold ............ A61B 17/12031 |
| 10,058,421 B2 | 8/2018 | Eberhardt et al. |
| 10,076,428 B2 | 9/2018 | Gorochow |
| 10,143,551 B2 | 12/2018 | Braido et al. |
| 10,182,927 B2 | 1/2019 | Lorenzo |
| 10,206,796 B2 | 2/2019 | Tehrani et al. |
| 10,232,564 B2 * | 3/2019 | Pel ........................ A61F 2/2412 |
| 10,292,851 B2 | 5/2019 | Gorochow |
| 10,321,991 B2 | 6/2019 | Glimsdale |
| 10,561,509 B2 | 2/2020 | Slazas et al. |
| 10,821,008 B2 | 11/2020 | Gorochow |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0188344 A1 | 12/2002 | Bolea |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0236406 A1 | 11/2004 | Gregorich |
| 2004/0254637 A1 | 12/2004 | Vang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0137682 A1 | 6/2005 | Justino |
| 2005/0148866 A1 | 7/2005 | Gunderson |
| 2005/0228484 A1 | 10/2005 | Stephens et al. |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0064151 A1 | 3/2006 | Guterman |
| 2006/0064156 A1 | 3/2006 | Thistle |
| 2006/0069424 A1 | 3/2006 | Acosta |
| 2006/0195175 A1 | 8/2006 | Bregulla |
| 2006/0206202 A1 | 9/2006 | Bonhoeffer et al. |
| 2006/0212113 A1 | 9/2006 | Shaolian et al. |
| 2006/0271153 A1 | 11/2006 | Garcia |
| 2006/0271165 A1 | 11/2006 | Yip et al. |
| 2006/0287717 A1 | 12/2006 | Rowe |
| 2007/0005127 A1 | 1/2007 | Boekstegers |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0208409 A1 | 9/2007 | Quigley |
| 2007/0213810 A1 | 9/2007 | Newhauser |
| 2007/0219612 A1 | 9/2007 | Andreas |
| 2007/0219613 A1 | 9/2007 | Kao |
| 2007/0233223 A1 | 10/2007 | Styrc |
| 2007/0233224 A1 | 10/2007 | Leynov |
| 2007/0233228 A1 | 10/2007 | Eberhardt et al. |
| 2007/0238979 A1 | 10/2007 | Huynh |
| 2007/0255385 A1 | 11/2007 | Fenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0281350 A1 | 11/2008 | Sepetka |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0192588 A1 | 7/2009 | Shin |
| 2009/0198315 A1 | 8/2009 | Boudjemline |
| 2009/0234429 A1 | 9/2009 | Lau |
| 2009/0248133 A1 | 10/2009 | Bloom |
| 2009/0287145 A1 | 11/2009 | Cragg |

(56) References Cited

U.S. PATENT DOCUMENTS

| | | |
|---|---|---|
| 2009/0297582 A1 | 12/2009 | Meyer et al. |
| 2009/0306761 A1 | 12/2009 | Hebert et al. |
| 2009/0326640 A1 | 12/2009 | Yoshimura |
| 2010/0010619 A1 | 1/2010 | Tischler |
| 2010/0010622 A1 | 1/2010 | Lowe |
| 2010/0069948 A1 | 3/2010 | Veznedaroglu |
| 2010/0161028 A1 | 6/2010 | Chuter |
| 2010/0161036 A1 | 6/2010 | Pintor |
| 2010/0234935 A1 | 9/2010 | Bashiri |
| 2010/0249815 A1* | 9/2010 | Jantzen ............ A61B 17/22031 606/159 |
| 2010/0274282 A1 | 10/2010 | Olson |
| 2010/0292777 A1 | 11/2010 | Meyer |
| 2010/0298872 A1 | 11/2010 | Berndt |
| 2010/0324649 A1 | 12/2010 | Mattsson |
| 2010/0324651 A1 | 12/2010 | Holzer |
| 2010/0331972 A1 | 12/2010 | Pintor |
| 2011/0004237 A1 | 1/2011 | Schneider et al. |
| 2011/0060400 A1 | 3/2011 | Oepen |
| 2011/0137397 A1 | 6/2011 | Chan et al. |
| 2011/0184508 A2 | 7/2011 | Burmeister |
| 2011/0264186 A1* | 10/2011 | Berglund ................ A61F 2/86 623/1.11 |
| 2011/0307049 A1 | 12/2011 | Kao |
| 2012/0035714 A1 | 2/2012 | Ducke et al. |
| 2012/0041538 A1 | 2/2012 | White |
| 2012/0065728 A1* | 3/2012 | Gainor ................ A61F 2/2445 623/2.11 |
| 2012/0123529 A1 | 5/2012 | Levi |
| 2012/0168022 A1 | 7/2012 | Rasmussen |
| 2012/0191176 A1 | 7/2012 | Nagi |
| 2012/0197377 A1 | 8/2012 | Ditter |
| 2012/0271403 A1 | 10/2012 | Gries |
| 2012/0283768 A1 | 11/2012 | Cox et al. |
| 2012/0296418 A1* | 11/2012 | Bonyuet ................ A61F 2/2415 623/2.18 |
| 2013/0041454 A1 | 2/2013 | Dobson |
| 2013/0060323 A1 | 3/2013 | McHugo |
| 2013/0123901 A1 | 5/2013 | Connor |
| 2013/0144375 A1 | 6/2013 | Giasolli |
| 2013/0245745 A1 | 9/2013 | Vong et al. |
| 2013/0253572 A1 | 9/2013 | Molaei et al. |
| 2013/0274849 A1 | 10/2013 | Zaver |
| 2013/0345739 A1 | 12/2013 | Brady |
| 2014/0025161 A1 | 1/2014 | Stankus et al. |
| 2014/0135812 A1 | 5/2014 | Divino et al. |
| 2014/0200607 A1 | 7/2014 | Sepetka et al. |
| 2014/0200648 A1 | 7/2014 | Newell et al. |
| 2014/0277332 A1* | 9/2014 | Slazas ................ A61F 2/86 623/1.11 |
| 2014/0277360 A1 | 9/2014 | Girnary et al. |
| 2014/0277376 A1 | 9/2014 | Lorenzo |
| 2014/0277400 A1 | 9/2014 | Wainwright et al. |
| 2014/0336741 A1 | 11/2014 | Connor |
| 2015/0018458 A1 | 1/2015 | Ito |
| 2015/0025625 A1 | 1/2015 | Rylski et al. |
| 2015/0045831 A1 | 2/2015 | Allen |
| 2015/0119974 A1 | 4/2015 | Rothstein |
| 2015/0148882 A1 | 5/2015 | Ma et al. |
| 2015/0265400 A1 | 9/2015 | Eidenschink |
| 2015/0320556 A1 | 11/2015 | Levi |
| 2015/0374483 A1 | 12/2015 | Janardham et al. |
| 2016/0030155 A1 | 2/2016 | Cox et al. |
| 2016/0038280 A1 | 2/2016 | Morriss |
| 2016/0058524 A1 | 3/2016 | Tehrani et al. |
| 2016/0235561 A1 | 8/2016 | Wrobel et al. |
| 2016/0302949 A1 | 10/2016 | Nishigishi |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079813 A1 | 3/2017 | Bar et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0156734 A1 | 6/2017 | Griffin |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0196689 A1 | 7/2017 | Salahieh |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265870 A1 | 9/2017 | Kealey et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281375 A1 | 10/2017 | Longo |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290653 A1 | 10/2017 | Folan et al. |
| 2017/0290654 A1 | 10/2017 | Sethna |
| 2017/0290686 A1 | 10/2017 | Sirhan |
| 2017/0296324 A1 | 10/2017 | Argentine |
| 2017/0296325 A1 | 10/2017 | Marrocco et al. |
| 2017/0303939 A1* | 10/2017 | Greenhalgh ......... A61B 17/221 |
| 2017/0303942 A1 | 10/2017 | Greenhalgh et al. |
| 2017/0303947 A1* | 10/2017 | Greenhalgh .......... A61M 39/06 |
| 2017/0303948 A1* | 10/2017 | Wallace ......... A61B 17/320725 |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1* | 12/2017 | Wallace ................... A61F 2/90 |
| 2017/0348514 A1 | 12/2017 | Guyon et al. |
| 2018/0092766 A1 | 4/2018 | Gorochow |
| 2018/0125649 A1* | 5/2018 | Nasr ..................... A61F 2/2415 |
| 2018/0263794 A1 | 9/2018 | Slazas et al. |
| 2018/0333281 A1 | 11/2018 | Tehrani et al. |

(56) References Cited

U.S. PATENT DOCUMENTS

| | | |
|---|---|---|
| 2019/0015229 A1 | 1/2019 | Fukutaki |
| 2019/0021888 A1 | 1/2019 | Tehrani |
| 2019/0038404 A1 | 2/2019 | Iamberger |
| 2019/0038405 A1* | 2/2019 | Iamberger ............... B29C 39/10 |
| 2019/0053895 A1* | 2/2019 | Levi ..................... A61F 2/2418 |
| 2019/0053899 A1 | 2/2019 | Levi |
| 2019/0224008 A1 | 7/2019 | Bressloff |

FOREIGN PATENT DOCUMENTS

| | | |
|---|---|---|
| CN | 102100587 A | 6/2011 |
| CN | 102271620 A | 12/2011 |
| CN | 103330605 A | 10/2013 |
| CN | 103347466 A | 10/2013 |
| CN | 104042376 A | 9/2014 |
| CN | 104042380 A | 9/2014 |
| CN | 104582643 A | 4/2015 |
| CN | 105592826 A | 5/2016 |
| CN | 105832452 A | 8/2016 |
| DE | 202008014828 U1 | 2/2009 |
| DE | 102011015995 A1 | 10/2012 |
| DE | 10 2014 113836 A1 | 3/2016 |
| EP | 0701800 A1 | 3/1996 |
| EP | 0894505 A2 | 2/1999 |
| EP | 1488763 A2 | 12/2004 |
| EP | 1634546 A1 | 3/2006 |
| EP | 2545887 A1 | 1/2013 |
| EP | 2 777 642 A1 | 9/2014 |
| EP | 2777638 A1 | 9/2014 |
| EP | 2777649 A1 | 9/2014 |
| EP | 2915509 A1 | 9/2015 |
| EP | 3 311 782 A1 | 4/2018 |
| FR | 2939637 A1 | 6/2010 |
| JP | 3-503246 A | 7/1991 |
| JP | 11-57010 A | 3/1999 |
| JP | 11-57020 A | 3/1999 |
| JP | 2004-267750 A | 9/2004 |
| JP | 2013-541358 A | 11/2013 |
| JP | 2016-202248 A | 12/2016 |
| WO | WO 1989/008433 A1 | 9/1989 |
| WO | WO 95/05132 A1 | 2/1995 |
| WO | WO 99/43379 A1 | 9/1999 |
| WO | WO 2001/015632 A1 | 3/2001 |
| WO | WO 01/35864 A1 | 5/2001 |
| WO | WO 2001/058384 A1 | 8/2001 |
| WO | WO 2001/072240 A1 | 10/2001 |
| WO | WO 2005/087138 A1 | 9/2005 |
| WO | WO 2008/130530 A1 | 10/2008 |
| WO | WO 2012/082440 A1 | 6/2012 |
| WO | WO 2012/096687 A1 | 7/2012 |
| WO | WO 2013/126299 A1 | 8/2013 |
| WO | WO 2013/151793 A1 | 10/2013 |

OTHER PUBLICATIONS mig-welding.co.uk; Excerpt from with comment of Jun. 29, 2011 on pictures of welds.
mitcale.com; Welded connections excerpt, downloaded Dec. 6, 2012.
Navigate Tough Anatomy; brochure Copyright 2009; Codman & Shurtleff, Inc., 325 Paramount Drive, Raynham, Massachusetts.
Plug Weld Joining Two Plates; Excerpt from esabna.com, downloaded Dec. 6, 2012.

* cited by examiner

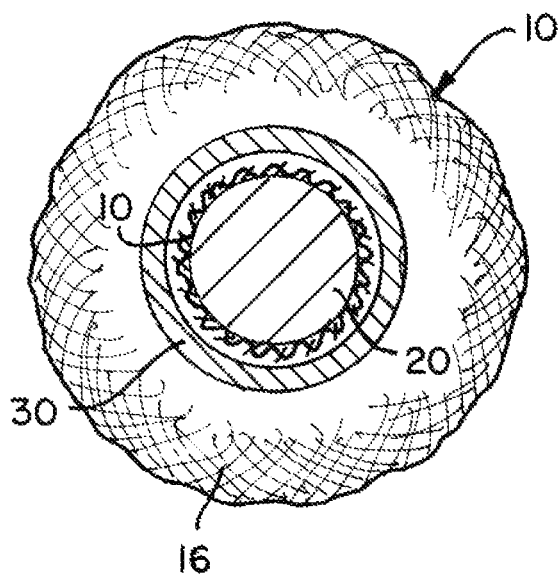
FIG. 5
FIG. 6
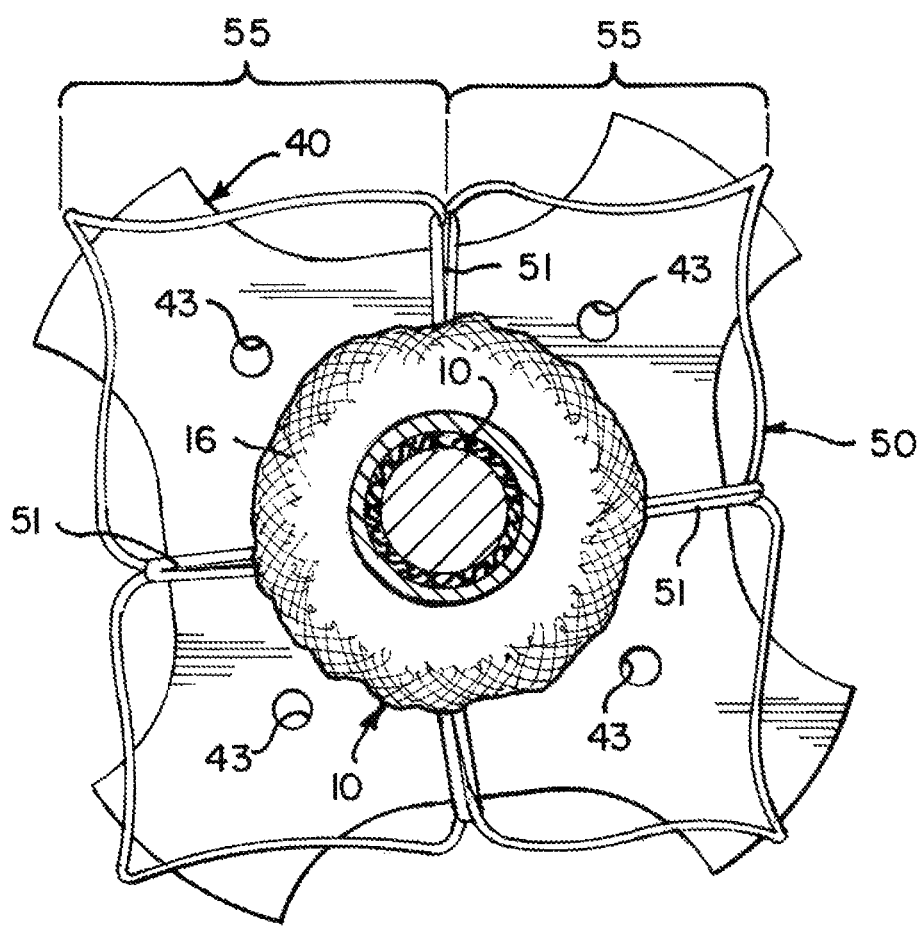

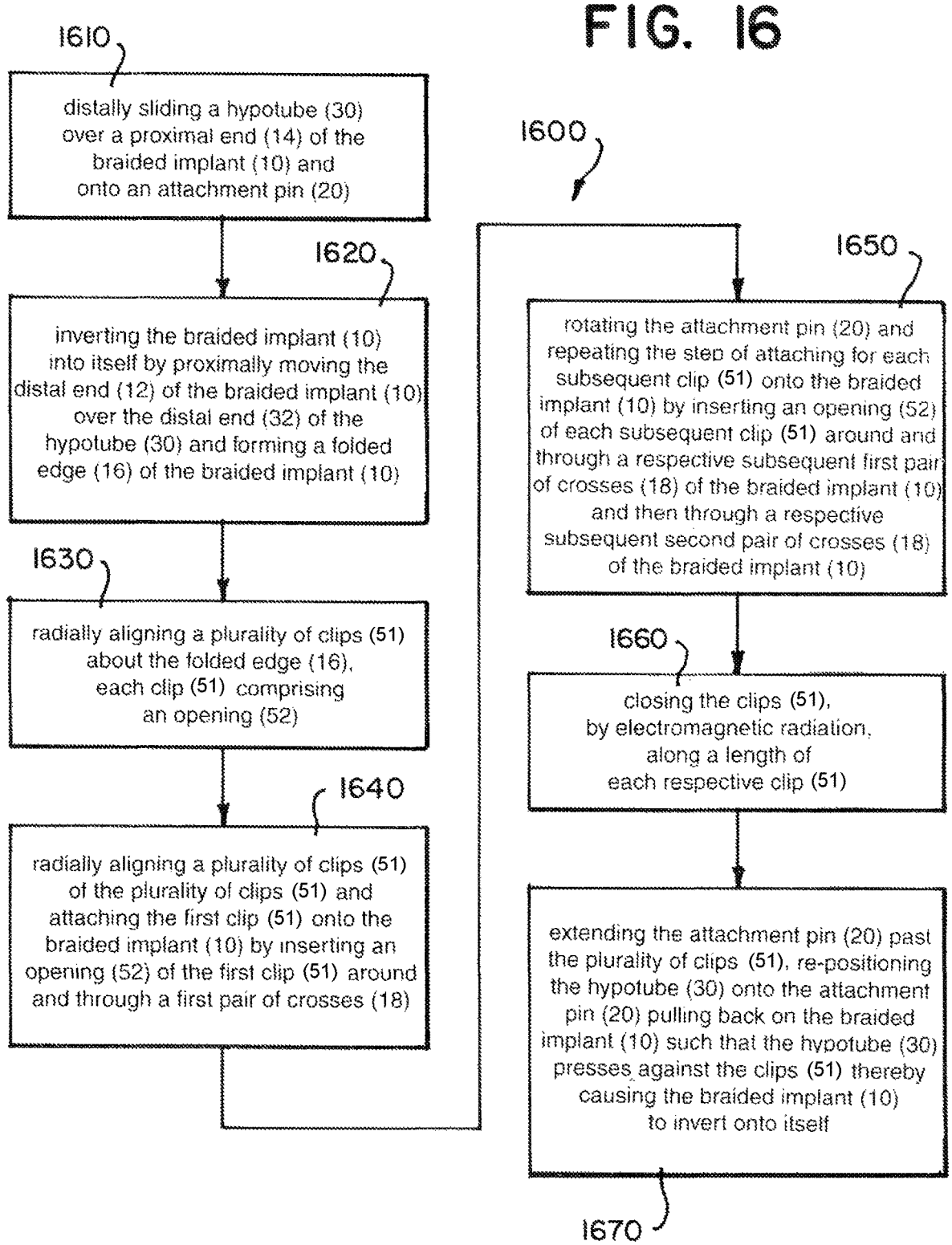

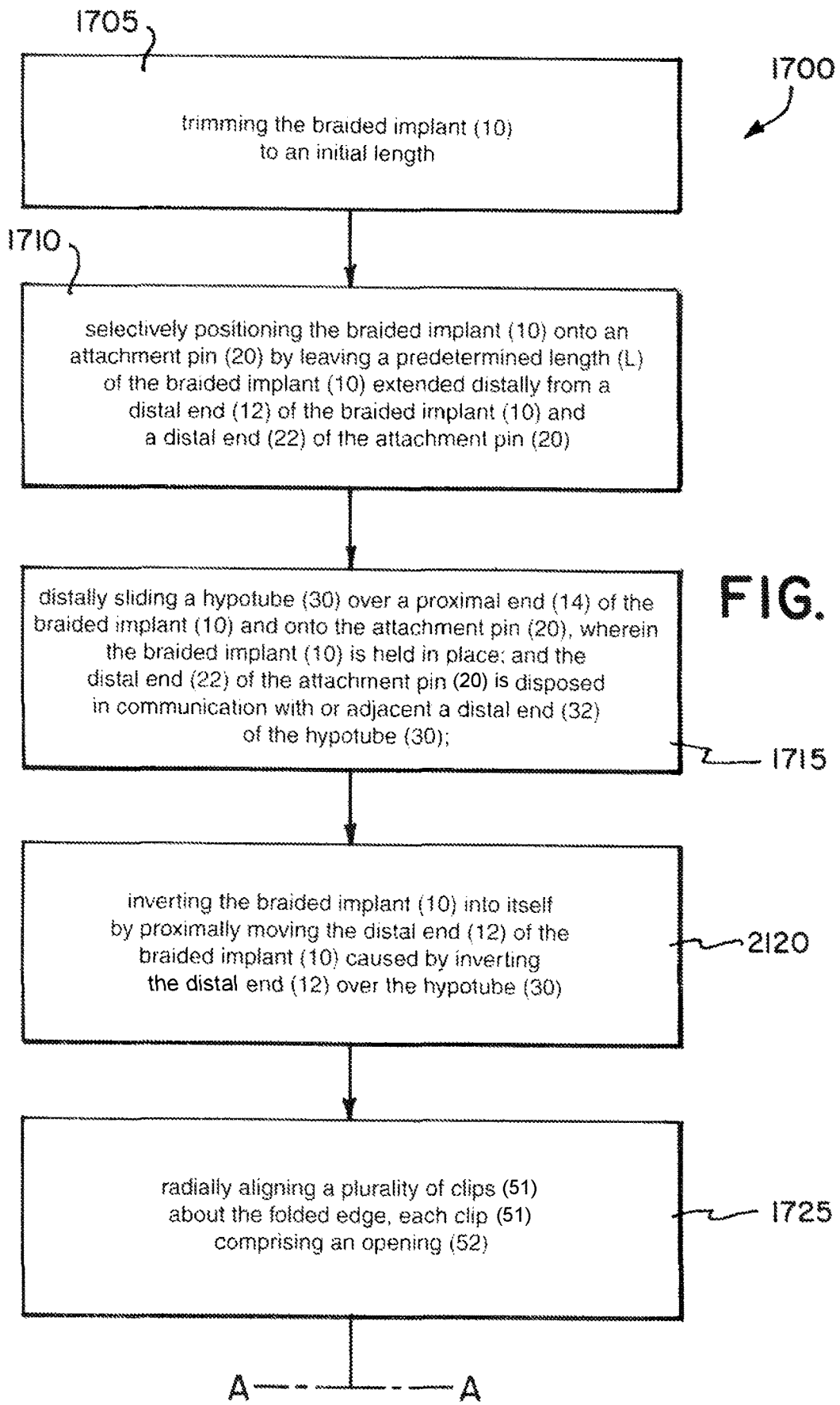

SYSTEMS AND METHODS OF MANUFACTURING AND USING AN EXPANSION RING

CROSS-REFERENCE TO RELATED APPLICATIONS

This application is a divisional of U.S. patent application Ser. No. 16/845,589 filed Apr. 10, 2020, which is a divisional of U.S. patent application Ser. No. 16/526,749, filed Jul. 30, 2019, now U.S. Pat. No. 10,646,361 issued May 12, 2020, which claims the benefit of priority of U.S. Provisional Patent Application No. 62/711,775, filed Jul. 30, 2018, the contents of all of which are incorporated herein by reference in their entirety.

FIELD

The present disclosure relates generally to treatment of certain defects in vasculature of a patient and more particularly, to delivering self-expanding braided stents to a treatment site in vasculature of a patient.

BACKGROUND

Braided stents used in clot retrieval devices are understood as tubular reinforcements that can be inserted into a blood vessel to provide an open path within the blood vessel. Such devices have been widely used in intravascular angioplasty treatment of occluded cardiac arteries, wherein the braid may be inserted after an angioplasty procedure to prevent restenosis of the artery. Braided stents are often deployed by use of delivery devices which cause them to open with the objective of reinforcing the artery wall and provide a clear through-path in the artery.

Further, the weakness and non-linear nature of the neurovasculature limits the applicability of such stents in procedures, for example, in repairing neurovascular defects. Furthermore, known delivery methods are less useful in vaso-occlusive surgery, particularly when tiny vessels, such as those found in the brain, are to be treated. Accordingly, there is a need for braided stents that can be used with delivery techniques in vaso-occlusive treatment of neurovascular defects that provides selective reinforcement in the vicinity of the neurovascular defect. There is also a need for a braided stent that reduces trauma or risk of rupture to the blood vessel. Finally, when braids are connected to expansion rings, some engineering challenges exist since such rings are usually internal and attached to the flow diverter braid mesh.

The solution of this disclosure resolves these and other issues of the art.

SUMMARY

Disclosed herein are various exemplary devices, systems, and methods of the present disclosure that can address the above needs. In one example, a braided implant is disclosed for flow diversion in the vasculature. The braided implant can be formed by a plurality of braided members with interstices being formed therebetween and include an expansion ring internally connected to the braided implant at a first end. The expansion ring can include a frame defined by a plurality of interconnected support leaves that are selectively positioned to impart an outwardly expanding radial force to the braided implant. Each leaf can include a plurality of legs that are joined at an intersection and connected to one of the other support leaves at an opposite intersection. A locking portion can be connected over a set of intersecting wires of the braided implant at respective circumferential locations on or adjacent the first end of the tube. An opening can be provided between the locking portion for connecting to the set of intersecting wires. The braided implant can be connected to the expansion ring by the following steps: positioning the braided implant about a tube; everting an end portion of the braided implant over a first end of the tube; assembling the expansion ring to the braided implant by pushing the opening of the leaves over the set of intersecting wires at respective circumferential locations on or adjacent the first end of the tube; closing the openings of each leaf over the set of intersecting wire; trimming ends of the braided implant; and reversing eversion of the braided implant thereby positioning the expansion ring internal to the braided implant.

In one example, the locking portion includes at least two aligned elongate members extended from the intersection with the opening formed therebetween.

In one example, a method of connecting an expansion ring to at least one end of a braided implant is disclosed. The method can include positioning the braided implant about a tube; everting an end portion of the braided implant over a first end of the tube; assembling an expansion ring to the braided implant, the expansion ring being a multi-leaved expansion ring comprising clips terminating with an open-ended coupling opening, wherein the openings are pushed over a set of intersecting wires of the braided implant at respective circumferential locations on or adjacent the first end of the tube; closing the openings over the set of intersecting wire; trimming ends of the braided implant; and reversing eversion of the braided implant thereby positioning the expansion ring internal to the braided implant.

In one example, the braided implant is a mesh flow diverter.

In one example, the end portion is retained about the tube using a silicone ring or sleeve.

In one example, each opening includes an elongated wider portion to accommodate wires of the braided implant.

In one example, the opening is approximately 1 mm long.

In one example, a method of manufacturing a braided implant for an aneurysm is disclosed. The method can include distally sliding a hypotube over a proximal end of the braided implant and onto an attachment pin; inverting the braided implant into itself by proximally moving the distal end of the braided implant over the distal end of the hypotube and forming a folded edge of the braided implant; radially aligning a plurality of clips of an expansion ring about the folded edge, each clip comprising an opening; gripping an inner surface of a first clip of the plurality of clips and attaching the first clip onto the braided implant by inserting an opening of the first clip around and through a first pair of crosses; rotating the attachment pin and repeating the step of attaching for each subsequent clip onto the braided implant by inserting an opening of each subsequent clip around and through a respective subsequent first pair of crosses of the braided implant and then through a respective subsequent second pair of crosses of the braided implant; welding the clips along a length of each respective clip and an inner surface of the braided implant; extending the attachment pin past the plurality of clips, repositioning the hypotube onto the attachment pin, and pulling back on the braided implant such that the hypotube presses against the clips thereby causing the braided implant to invert onto itself.

In one example, the plurality of clips of the expansion ring consists of four interconnected clips and the expansion ring includes adjoining upper and lower legs that form a four-leaved expansion ring.

In one example, each of the clips are welded by electromagnetic radiation at three separate locations located along the length of the respective clip and internal to the braided implant.

In one example, the method can include engaging each of the four clips with crosses that include a double round pair if the clips are disposed in a predetermined quadrant location.

In one example, each of the clips are welded by electromagnetic radiation at three separate locations located along a length of the respective clip and internal to the braided implant; and positioning the braided implant into a transport tube.

In one example, the method can include positioning a tip of at least one of the clips into the hypotube up to 0.5 mm.

In one example, the method can include forming a symmetric pattern with each clip having a mirror image on opposite sides of the braided implant.

In one example, the method can include loading the braided implant into a fixture; and placing the fixture over the braided implant.

In one example, the fixture includes four quadrants corresponding to openings of the clip, and wherein the step of rotating the attachment pin includes rotating the attachment pin from one quadrant to the next.

In one example, a method of manufacturing a braided implant for an aneurysm is disclosed. The method can include trimming the braided implant to an initial length; selectively positioning the braided implant onto an attachment pin by leaving a predetermined length (L) of the braided implant extended distally from a distal end of the braided implant and a distal end of the attachment pin; distally sliding a hypotube over a proximal end of the braided implant and onto the attachment pin. The braided implant is held in place and the distal end of the attachment pin is disposed in communication with or adjacent a distal end of the hypotube. The method can also include inverting the braided implant into itself by proximally moving the distal end of the braided implant over the distal end of the hypotube; positioning the attachment pin such that the braided implant is disposed vertically aligned with a microscope to view a folded edge of the braided implant caused by inverting the distal end of the braided implant over the hypotube; radially aligning an expansion ring comprising a plurality of clips about the folded edge, each clip comprising an opening; gripping, by a gripping mechanism, an inner surface of a first clip of the plurality of clips; attaching the first clip onto the braided implant by inserting an opening of the first clip around and through a first pair of crosses of the braided implant; rotating the attachment pin and attaching a subsequent clip onto the braided implant by inserting an opening of the subsequent clip around and through a subsequent first pair of crosses of the braided implant and then through a subsequent second pair of crosses of the braided implant; positioning the attachment pin and braided implant under electromagnetic radiation so that the respective opening of each clip is aligned with the crosses; closing the clips, by the electromagnetic radiation, along a length of each respective clip and internal to the braided implant; extending the attachment pin past the plurality of clips, repositioning the hypotube onto the attachment pin, and pulling back on the braided implant such that the hypotube presses against the clips thereby causing the braided implant to invert onto itself.

In one example, the plurality of clips consists of four clips that form the expansion ring comprising four-leaves. The method in this embodiment can include rotating the attachment pin and attaching a third clip of the plurality of clips onto the braided implant by inserting an opening of the third clip around and through a first pair of crosses of the braided implant adjacent the third clip and then through a subsequent second pair of crosses of the braided implant adjacent the third clip; and rotating the attachment pin and attaching a fourth clip of the plurality of clips onto the braided implant by inserting an opening of the fourth clip around and through a first pair of crosses of the braided implant adjacent the fourth clip and then through a subsequent second pair of crosses of the braided implant adjacent the fourth clip.

In one example, the method can include engaging each of the four clips with crosses that include a double round pair if the clips are disposed in a predetermined quadrant location.

In one example, the method can include repeating the steps of extending the attachment pin past the plurality of clips, repositioning the hypotube onto the attachment pin, and pulling back on the braided implant for each of the plurality of clips to complete this unit.

In one example, the method can include closing each of the clips by electromagnetic radiation at three separate locations located along the length of the respective clip and along an inner surface of the braided implant, and positioning the braided implant into a transport tube.

In one example, each of the respective crosses are adjacent the respective clip to the braided implant.

In one example, the method can include positioning a tip of at least one of the clips into the hypotube up to 0.5 mm.

In one example, the method can include trimming the braided implant by using a straight edge ruler.

In one example, the method can include forming a symmetric pattern with each clip having a mirror image on opposite sides of the braided implant.

In one example, the method can include a Rofin laser applying the electromagnetic radiation.

In one example, the initial length is selected by determining a diameter of the braided implant; and determining the initial length appropriate for the braided implant by referring to a table of initial lengths sorted by diameter.

In one example, the predetermined length (L) is approximately 10 mm.

In one example, the method can include loading the braided implant into a fixture and placing the fixture over the braided implant.

In one example, the fixture includes four quadrants corresponding to openings of the clip, and wherein the step of rotating the attachment pin includes rotating the attachment pin from one quadrant to the next.

In one example, the gripping mechanism is a pair of tweezers.

In one example, the gripping mechanism includes a pair of levers connected at one fixed end and a pair of pincers at an opposite end.

In one example, the first pair of crosses is a double round engagement and the second pair of crosses is a double platinum. In another example, the first pair of crosses is a double round and the second pair of crosses is a round engagement in the first location of engagement.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 5 depicts a forward cross-sectional view of one step of the method shown beginning in FIGS. 1-2.

FIG. 6 depicts a forward plan view of one step of the method shown beginning in FIGS. 1-2 whereby an example braid is assembled with a fixture.

FIG. 16 depicts flow diagrams outlining example method steps of this disclosure.

FIGS. 17a to 17c depict flow diagrams outlining example method steps of this disclosure.

DETAILED DESCRIPTION

Figure 1:
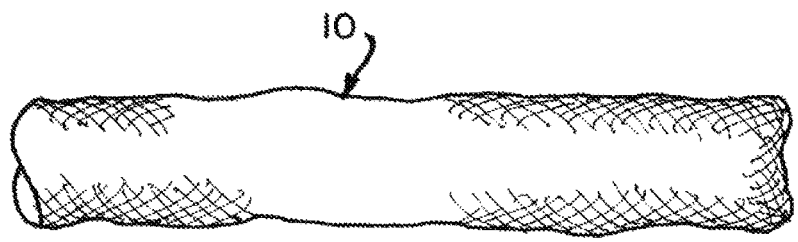
FIG. 1 depicts a side plan view of one step of a method of this disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

In braided implant delivery systems, it can be advantageous to incorporate selective reinforcement in the vicinity of the neurovascular defect through one or more expansion rings of this disclosure that are assembled with a braided implant, as described more particularly herein. In one example, a method of connecting an expansion ring to at least one end of a braided implant is disclosed. The method can include positioning the braided implant about a tube; everting an end portion of the braided implant over a first end of the tube; assembling an expansion ring to the braided implant, the expansion ring being a multi-leaved expansion ring including clips terminating with an open-ended coupling opening. The openings can be pushed over a set of intersecting wires of the braided implant at respective circumferential locations on or adjacent the first end of the tube. The method can also include closing the openings over the set of intersecting wire; trimming ends of the braided implant; and reversing eversion of the braided implant thereby positioning the expansion ring internal to the braided implant. This method can be better understood when looking at the figures appended to this disclosure.

In FIG. 1, an example braid 10 is depicted being cut to an initial length using an example straight edge metric scale 80. A practitioner can consult a table that guides the determination of the initial length according to the particular braid 10 diameter. Braid 10 may be formed from a plurality of elongate members braided or otherwise arranged to form a plurality of interstices. Elongate members may be formed from two or more metal wires, or polymeric fibers or strands of material.

Figure 2:
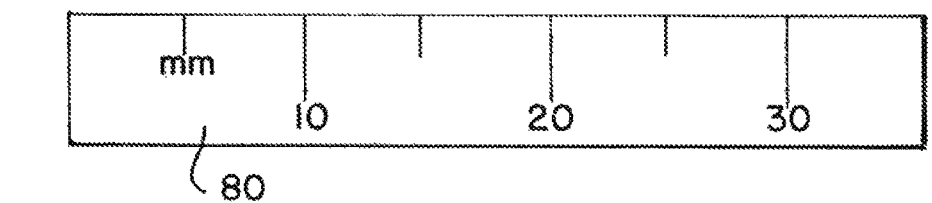
FIG. 2 depicts a side plan view of one step of a method of this disclosure.

In FIG. 2, the example braid 10 is depicted from FIG. 1 now placed onto attachment pin 20. Attachment pin 20 can be a nitinol segment attachment pin that includes a proximal end 24 and a distal end 22. As can be seen, braid 10 may comprise a proximal end 14 and a distal end 12. A length L of separation may be provided between distal end 22 and distal end 12. Braid 10 and pin 20 are each shown with a break to represent indeterminate length since FIG. 2 is not intended to limit the contemplated scope, including length of either braid 10 or pin 20, and instead either can have any number of dimensions according to need or preference. Anywhere else in this disclosure where similar breaks are depicted with respect to certain features, similar scope is contemplated for that respective feature.

Figure 3:
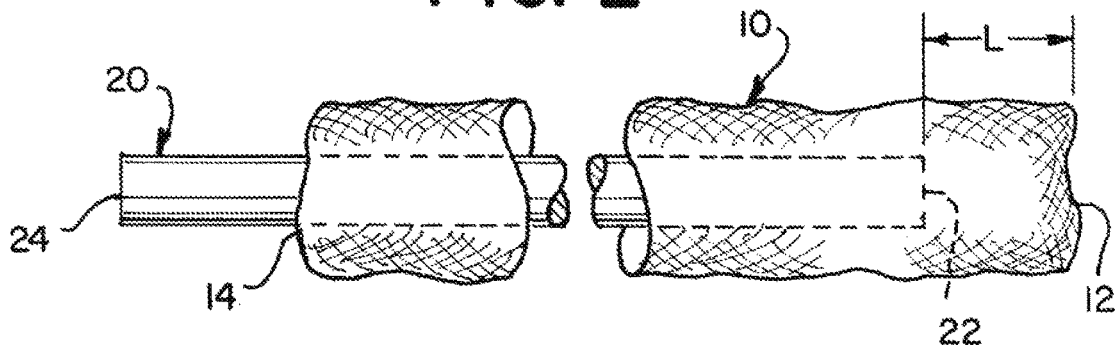
FIG. 3 depicts a side plan view of one step of the method shown beginning in FIGS. 1-2.

In FIG. 3, a side plan view of one step of the method begun in FIGS. 1-2 is shown. The example braid 10 is depicted still placed onto attachment pin 20 with a hypotube 30 positioned over both braid 10 and pin 20. Hypotube 30 can include a distal end 32 and proximal end 34. Hypotube 30 can be slid over the proximal end 14 of braid 10 and proximal end 24 of pin 20 so that the braid 10 is held in place while proximal end 24 is aligned (e.g., flush) with proximal end 24 of hypotube 30. In contrast, distal end 12 of braid 10 can extend distally past distal ends 22 and 32 leaving a length L. Length L can be approximately 10 mm of braid 10 that extends past the end of pin 20, though other lengths can be used and are contemplated within the scope of this disclosure. The portion of braid 10 with length L in FIG. 3 can be arcuate and expand from smaller to larger diameter as braid 10 exits distal end 22 to distal end 12. It can be seen that FIG. 3 includes a plane 5-5 proximal of distal end 32 that runs across pin 20, hypotube 32 and braid 10 as will be discussed more particularly below in FIG. 5.

Figure 4:
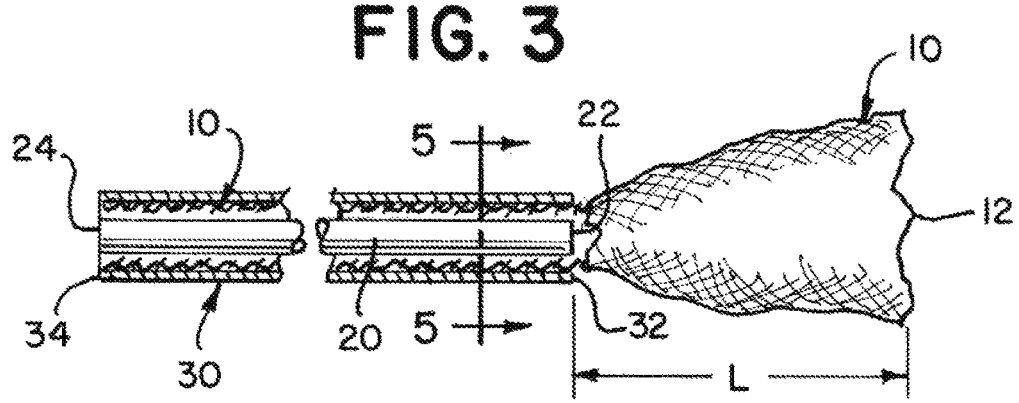
FIG. 4 depicts a side plan view of one step of the method shown beginning in FIGS. 1-2.

In FIG. 4, a side plan view of one step of the method begun in FIG. 2 is shown. The example braid 10 is depicted still placed onto attachment pin 20 with a hypotube 30 positioned over both braid 10 and pin 20. In this example, the braid 10 has been rolled proximally such that it is inverted onto itself about distal end 32 of hypotube 30. Distal end 12 in particular has been proximally translated along the outer surface of hypotube 30 after inverting over distal end 32, while attachment pin 20 remains disposed internal thereto. Proximal end 14 of braid 10 also extends proximally from proximal end 34 to an expanded diameter greater than the outer diameter of hypotube 30. In certain examples, the braid 10 is inverted into itself by proximally moving the distal end 12 over the distal end 32 of the hypotube 30 and forming a folded edge 16 thereabout.

In FIG. 5, a forward plan view of one step of the method begun in FIG. 2 is shown. In particular, FIG. 5 is a forward cross-sectional plan view at section 5-5 of FIG. 3 showing example braid 10 with folded edge 16 of braid 10 axially aligned with pin 20 and hypotube 30. It can be seen that the inverted outer diameter of edge 16 is larger than diameters of pin 20 and hypotube 30. It can be seen that the pin 20 is positioned such that the braid is sitting vertically (e.g., visible underneath a microscope) that in turn permits full viewing of the edge 16. Edge 16 also forms an extended atraumatic three-dimensional edge in this view as edge 16 extends distally of hypotube 30 and pin 20.

In FIG. 6, a forward plan view of one step of the method begun in FIG. 2 is shown. In FIG. 6, example braid 10 is depicted with folded edge 16 of braid 10 axially aligned with pin 20 and hypotube 30, similar to FIG. 5. However, it can also be seen that expansion ring 50 is now being assembled with braid 10 as discussed more particularly below. Ring 50 may be constructed from a plurality of interconnected leaves 55 that together form a frame of ring 50 capable of imparting one or more additive radial forces to an inner wall and/or an outer wall of the lumen of braid 10. This disclosure discusses approaches for assembling one or more rings 50 with braid 10 that is reliable with reduced risk of injury for the end-user during use.

In particular, ring 50 is loaded into fixture 40 and fixture 40 in turn is placed over braid 10. Optionally, ring 50 can be loaded into fixture 40 by aligning each leaf 55 with respective alignment apertures 43. However, it is understood that examples of this disclosure may not necessarily require fixture 40. Ring 50 can be internally connected to braid 10 at the distal end 12, as shown. Ring 50 can include a frame that is defined by a plurality of interconnected support leaves 55. Each leaf 55 can be selectively positioned to impart an outwardly expanding radial force to the braided implant 10 when moving between collapsed to expanded configurations during use.

Each leaf can include a plurality of legs 58, 59 that can be joined at an intersection (see e.g., FIG. 11), and connected to one of the other support leaves 55 of ring 50, at an opposite intersection. While FIG. 6 depicts ring 50 having four (4) leaves 55, it is contemplated that ring 50 can include fewer or greater number of leaves 55 as needed or required. Leaf 55 may include a locking portion 56, 54 as well as clip 51, as more clearly shown in FIG. 8, whereby clip 51 engages with the braid 10 while also having its adjoining legs 58, 59 aligned with each quadrant of fixture 40. While only quadrants are depicted in the example of fixture in FIG. 6, it is contemplated that fixture 40 could have any number of portions as needed or required according to respective expansion ring 50.

It can be seen that the inverted outer diameter of edge 16 is larger than diameters of pin 20 and hypotube 30. It can be seen that the pin 20 is positioned such that the braid is sitting vertically (e.g., visible underneath a microscope) that in turn permits full viewing of the edge 16. Edge 16 also forms an extended atraumatic three-dimensional end in this view as edge 16 extends distally of hypotube 30 and pin 20.

Figure 7:
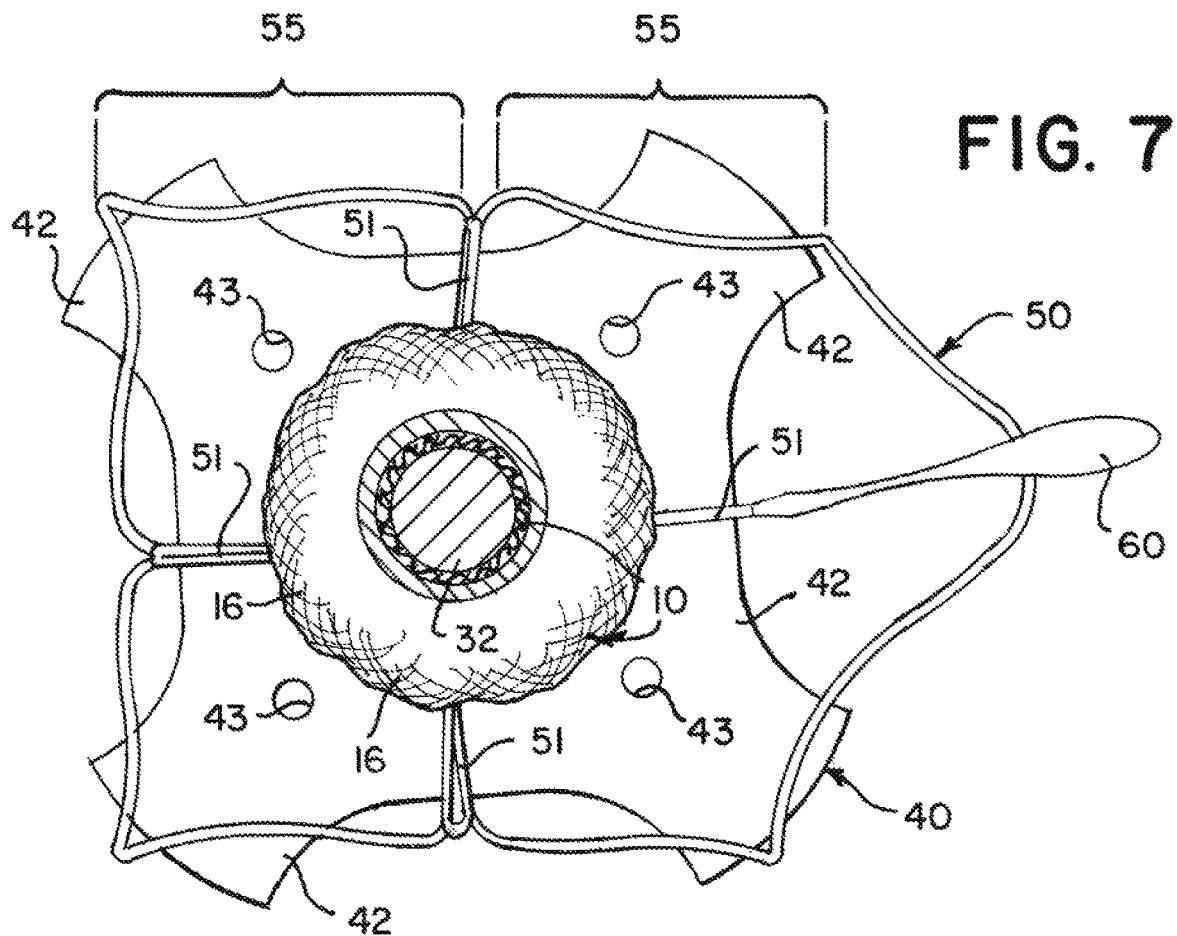
FIG. 7 depicts a forward plan view of one step of the method shown beginning in FIGS. 1-2 whereby an example braid is assembled with a fixture.

In FIG. 7, a forward plan view of one step of the method begun in FIG. 2 is shown, similar to FIG. 6. Braid 10 is depicted in a forward plan view with folded edge 16 of braid 10 axially aligned with pin 20 and hypotube 30. As can be seen, one of clips 51 of ring 50 is being gripped or engaged on its inside face using a gripping mechanism 60 (e.g., tweezers or mechanism including a pair of levers connected at one fixed end and a pair of pincers at an opposite end). Once engaged, clip 51 can be attached onto braid 10 by inserting an opening 52 of clip 51 around and through a first pair of crosses 18. This can be implemented by pulling or otherwise moving portions of clip 51 as depicted in FIG. 7. Crosses 18 engaged with clip 51 can include one or more of the following combination of flat/round, flat/flat, round/flat, or flat/round wire crosses. Once passed therethrough, clip 51 can be guided back up through the next cross 18 of wires of braid 10. In some examples, it is acceptable to engage clip 51 on a double round cross 18 (e.g., platinum or otherwise radiopaque material).

Figure 8:
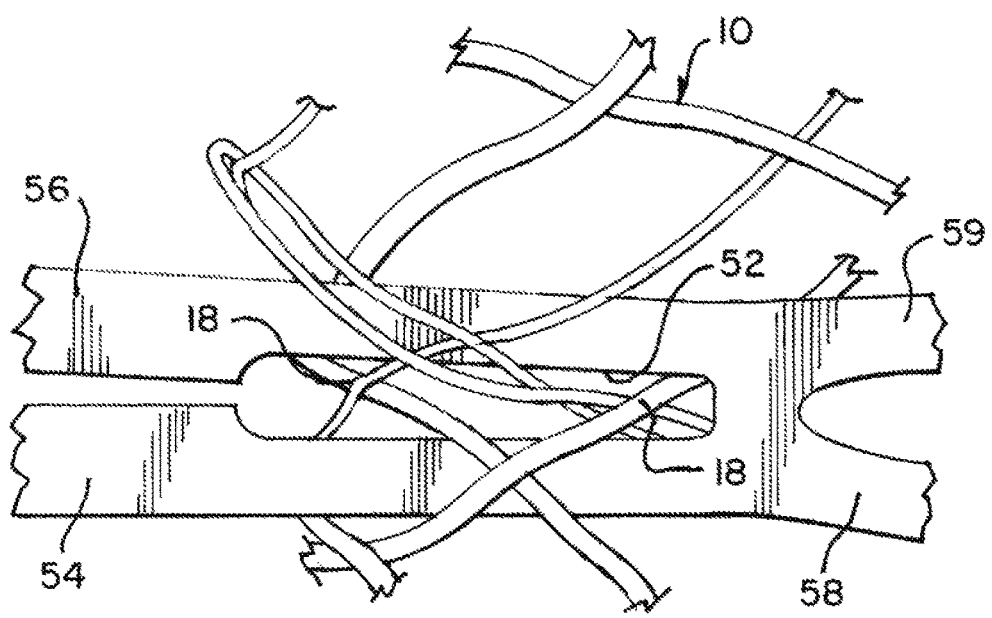
FIG. 8 depicts a close-up view of engaged crosses of this disclosure in communication with an example clip.

In FIG. 8, a side plan view of a close-up of braid 10 with engaged crosses 18 interwoven with portions of clip 51 is shown. Specifically, it can be seen that upper 56 and lower 54 locking portions are connected over a set of intersecting wires 18 of braid 10 at respective circumferential locations. Prior to the view shown in FIG. 8, ring 50 is assembled to braid 10 by pushing the opening 52 over intersecting wires 18 at respective circumferential locations and then closing the opening 52 (e.g., crimping portions 56 and 54 together). Portions 54, 56 may include two aligned members 53 that are elongate and extended away from respective intersection(s) on opening 52 and opposite portions 54, 56. In some examples, members 53 are aligned in parallel and taper or become thinner about opening 52 and then thicken at portions 54, 56. Portions 56 and 54 can be connected together through one or more crimpings, welds, soldered connections, chemical adhesive or the like. The shape and/or pattern of clip 51 may be laser cut into the metal alloy tube of ring 50. However, ring 50 is not so limited and the clip pattern may be formed into one end of the metal alloy tube by any other manufacturing technique as needed or required including 3-d printing, a CNC machine, a lather, additive manufacturing, etc.

It can be seen in FIG. 8 that two separate crosses 18 are depicted being connected over opening 52 formed when portions 54, 56 are connected to each other. However, fewer or greater number of crosses 18 are contemplated as embodiments of this disclosure. Intersecting wires 18 can also be disposed on or adjacent the first end 22 of pin 20. Opening 52 is depicted being defined between locking portion 56, 54. The crosses 18 shown in FIG. 8 can include a double round cross on the left and a flat cross shown on the right, which is an acceptable engagement according to this example.

Figure 9:
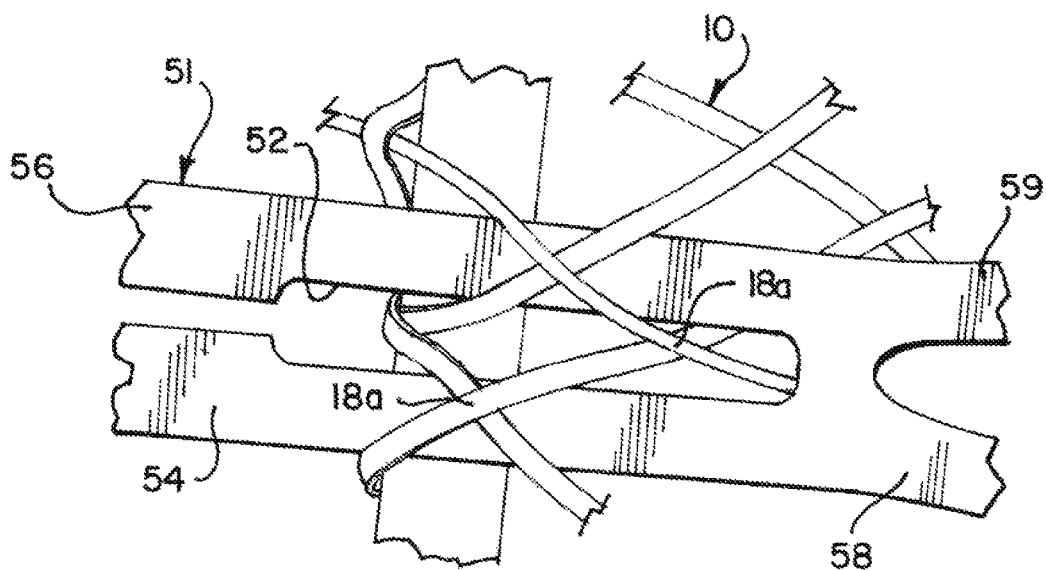
FIG. 9 depicts a close-up view of engaged crosses of this disclosure in communication with an example clip.

In FIG. 9, similar to FIG. 8, a side plan view of a close-up of braid 10 with another example of engaged crosses 18 interwoven with portions of clip 51 is shown. The crosses 18 shown in FIG. 9 can include a double round cross on the right and a round engagement in the cross on the left, which is an acceptable engagement according to this example.

Figure 10A:
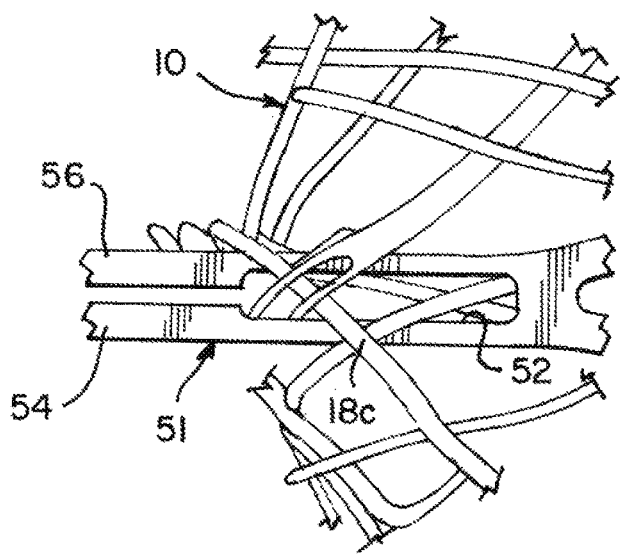
FIG. 10a depicts a close-up view of engaged crosses with an example clip according to this disclosure.
Figure 10B:
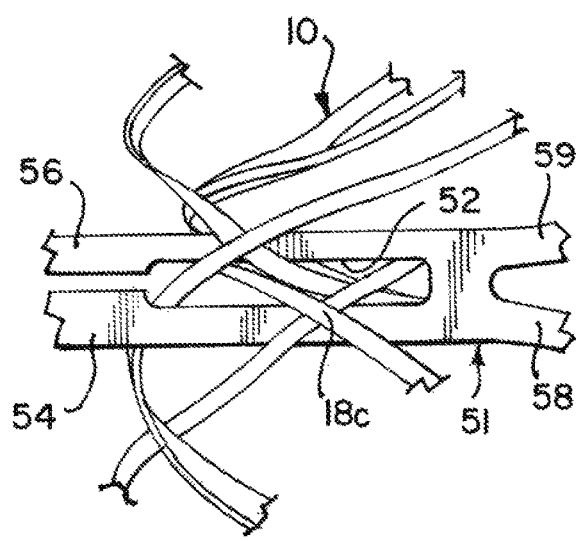
FIG. 10b depicts a close-up view of engaged crosses with an example clip according to this disclosure.

In FIGS. 10a and 10b, side plan views are shown depicting a close-up of braid 10 with another example of engaged crosses 18 interwoven with portions of clip 51. In FIG. 10a, a double round engagement is shown in the second cross 18. In FIG. 10b, a double round engagement is shown in the first cross 18. The configuration of crosses 18 shown in FIGS. 10a and 10b is deemed unacceptable and outside of the process of manufacturing the braid 10 with corresponding ring 50, as described herein.

Figure 11:
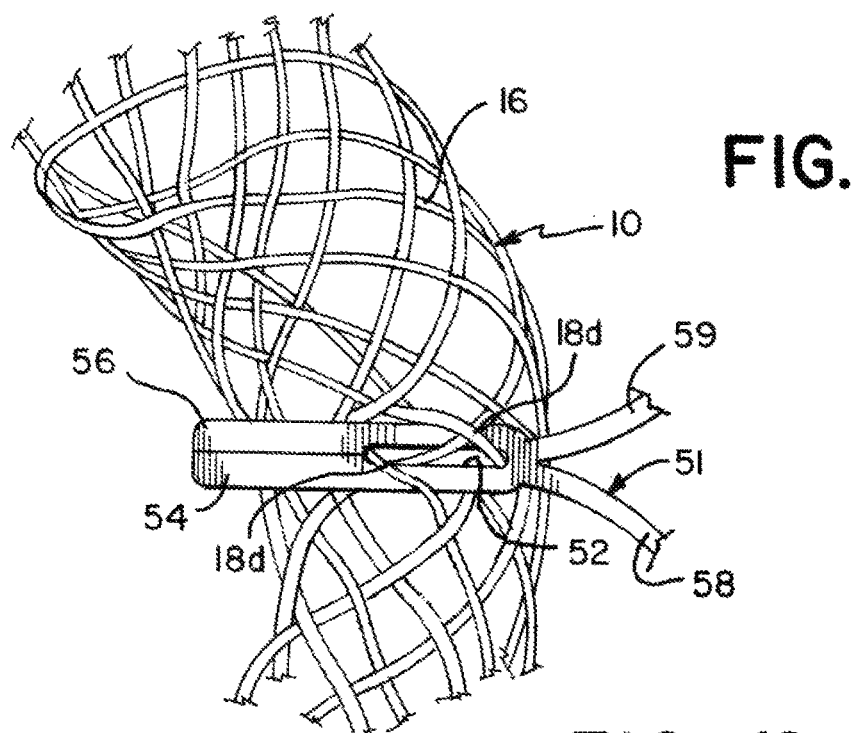
FIG. 11 depicts a close-up perspective view of engaged crosses of this disclosure in communication with an example clip.

In FIG. 11, a side plan view of a close-up of braid 10 with another example of engaged crosses 18 interwoven with portions of clip 51 is shown. In this view, edge 16 can be seen extending in a curved, inverted configuration from distal end 34 of hypotube 30 with clip 51 engaged therewith. In particular, upper leg 59 and lower leg 58 of clip 51 are connected together at an intersection from which upper 56 and lower 54 elongate portions of clip 51 extend and ultimately connect. The crosses 18d shown in FIG. 11 can include a flat, flat cross on the first engagement on the left and a round, round cross in the second engagement on the right, which is an acceptable engagement according to this example.

Figure 12:
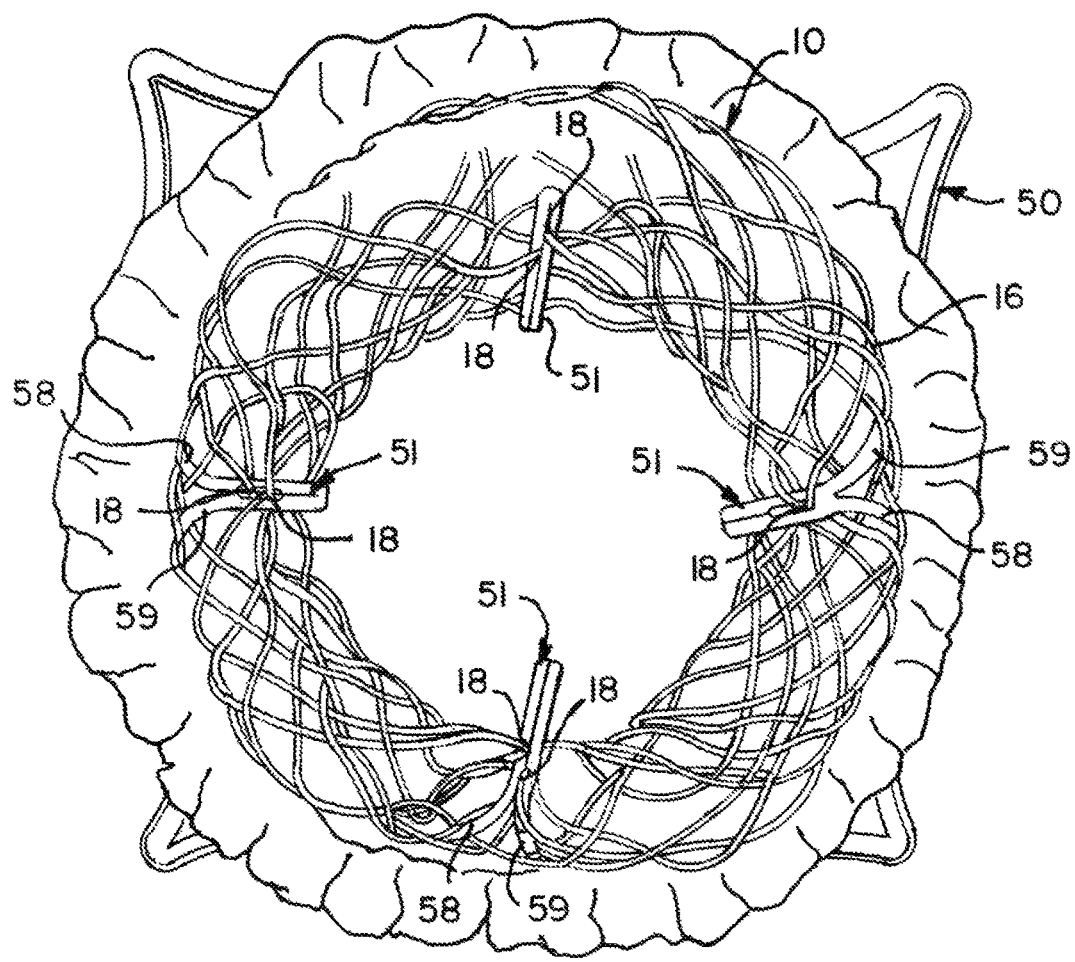
FIG. 12 depicts a close-up perspective view of engaged crosses of this disclosure in communication with a plurality of example clips.

In FIG. 12, a forward plan view of a close-up of braid 10 with an example of a plurality of engaged crosses 18 interwoven with clips 51 is shown. In this view, pin 20 has been rotated from one quadrant of ring 50 to the next so the subsequent clip 51 of ring 50 can be attached to braid, according to this disclosure. In certain examples, appropriate placement of clips 51 with respect to braid 10 will produce a symmetric pattern with each clip 51 having a mirror image of itself on the other side of the braid 10. This rotation and attachment process can then be repeated for all respective clips 51 of ring 50. When finished, all clips 51 can be positioned sufficiently engaged through the braid 10 via the respective crosses 18. In certain examples, it may be acceptable for the tips of clip 51 (e.g., tips of portions 54, 56) to slip into the hypotube 30 a certain predetermined depth (e.g., up to 0.5 mm).

In certain examples it is acceptable for any of clips 51 to engage on a double round cross 18 if it resides in the optimum quadrant location with respect to ring 50 and/or corresponding fixture 40. However, it is not acceptable to have a clip 51 engage on a cross 18 that includes two double round pairs (i.e. 4 wires).

Figure 13:
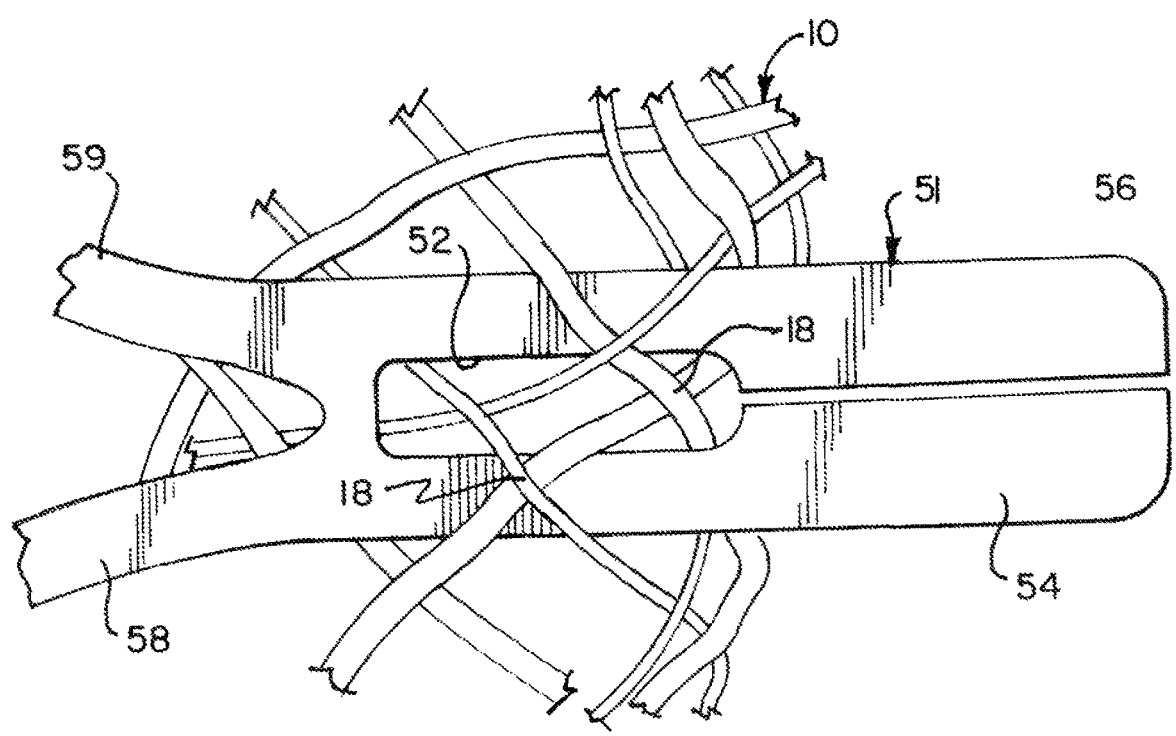
FIG. 13 depicts a close-up view of engaged crosses of this disclosure in communication with an example clip.

In FIG. 13, a side plan view of a close-up of braid 10 with another example of engaged crosses 18 interwoven with portions of clip 51 is shown. In this example, attachment pin 20 has been placed along with the braided implant 10 and engaged crosses 18 under a Rofin laser such that the opening 52 in the clip 50 is underneath the engaged crosses 18, as depicted.

Figure 14:
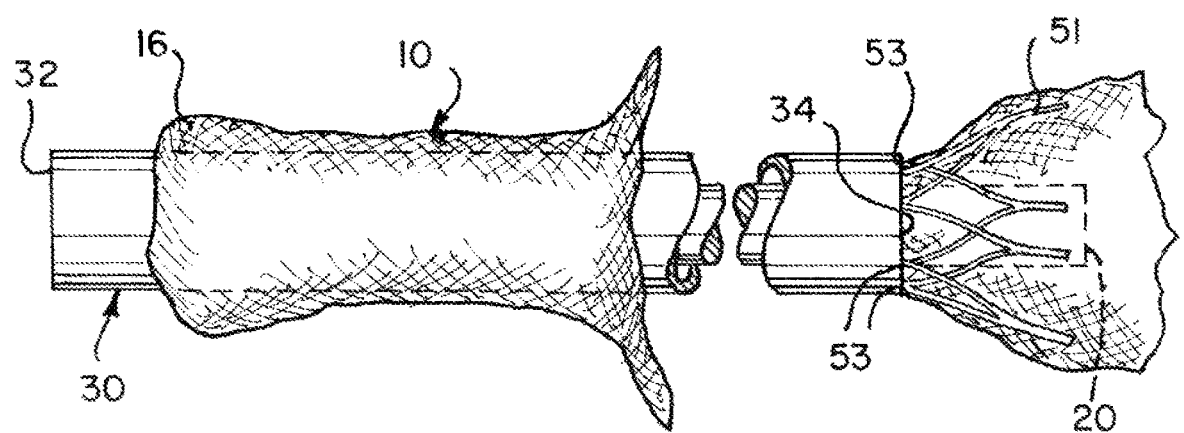
FIG. 14 depicts a forward plan view of one step of the method shown beginning in FIGS. 1-2.

In FIG. 14, braid 10 is depicted again on pin 20. In this view, all connections of clips 51 have been inspected such that braid 10 can be flipped back to its original position. In this respect, pin 20 can extend past the clips 51 and then be pulled back on braid 10 so that hypotube 30 is abutting or in contact or otherwise against clips 51 (e.g., at the tips of clips 51). Braid 10 can be rolled back to cause it to invert onto itself, as shown.

Figure 15:
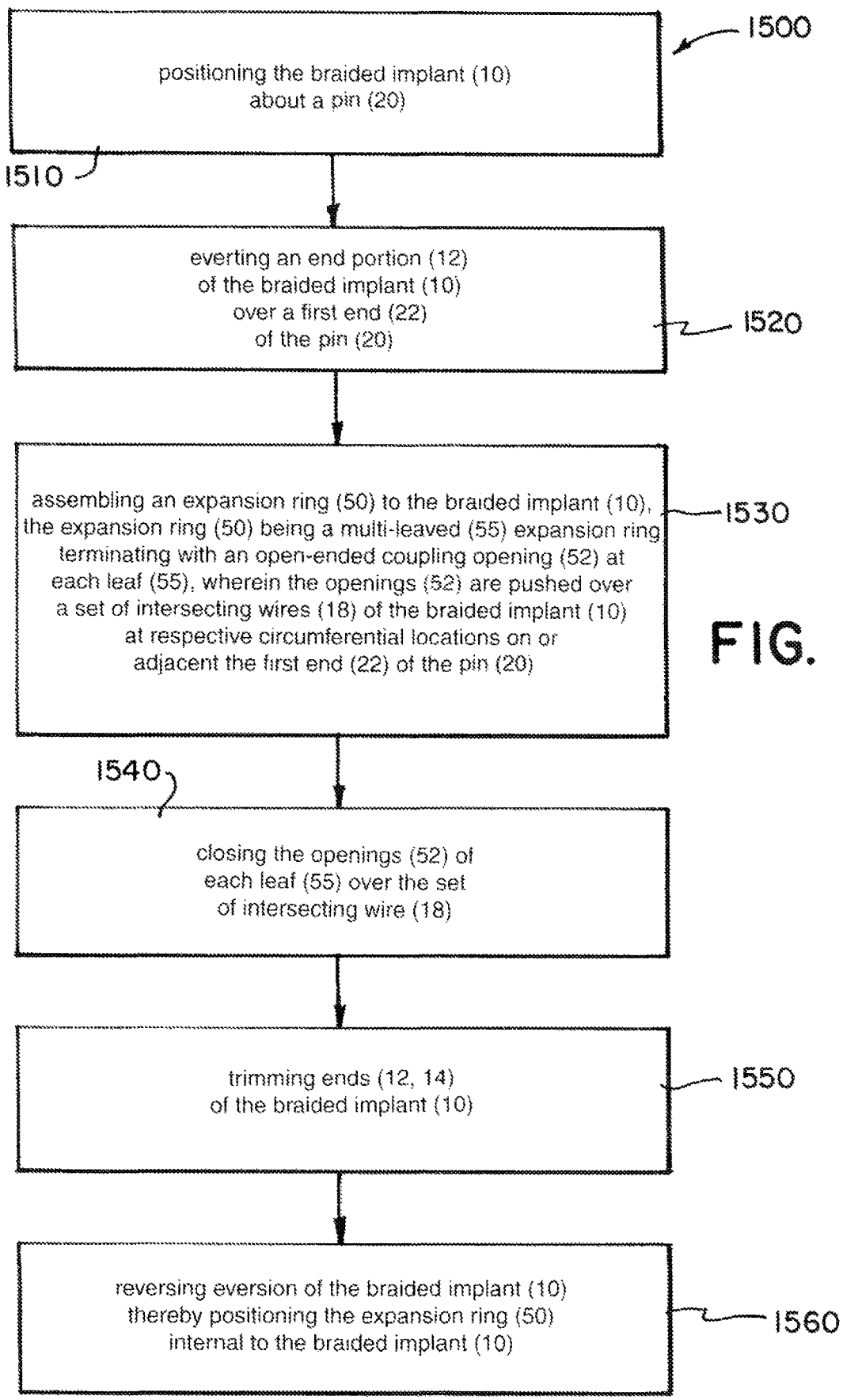
FIG. 15 depicts flow diagrams outlining example method steps of this disclosure.

Turning to FIG. 15, a schematic overview of one method 1500 of this disclosure is shown. Method 1500 can include step 1510 positioning the braided implant (10) about a pin (20). Method 1500 can also include step 1520 everting an end portion (12) of the braided implant (10) over a first end (22) of the pin (20). Method 1500 can also include step 1530 assembling an expansion ring (50) to the braided implant (10), the expansion ring (50) being a multi-leaved (55) expansion ring terminating with an open-ended coupling opening (52) at each leaf (55), wherein the openings (52) are pushed over a set of intersecting wires (18) of the braided implant (10) at respective circumferential locations on or adjacent the first end (22) of the pin (20). Method 1500 can also include step 1540 closing the openings (52) of each leaf (55) over the set of intersecting wire (18). Method 1500 can also include step 1550 trimming ends (12, 14) of the braided implant (10). Method 1500 can also include step 1560 reversing eversion of the braided implant (10) thereby positioning the expansion ring (50) internal to the braided implant (10).

Turning to FIG. 16, a schematic overview of one method 1600 of this disclosure is shown. Method 1600 can include step 1610 distally sliding a hypotube (30) over a proximal end (14) of the braided implant (10) and onto an attachment pin (20). Method 1600 can also include step 1620 inverting the braided implant (10) into itself by proximally moving the distal end (12) of the braided implant (10) over the distal end (32) of the hypotube (30) and forming a folded edge (16) of the braided implant (10). Method 1600 can also include step 1630 radially aligning a plurality of clips (51) about the folded edge (16), each clip (51) comprising an opening (52). Method 1600 can also include step 1640 gripping an inner surface of a first clip (51) of the plurality of clips (51) and attaching the first clip (51) onto the braided implant (10) by inserting an opening (52) of the first clip (51) around and through a first pair of crosses (18).

Method 1600 can also include step 1650 rotating the attachment pin (20) and repeating the step of attaching for each subsequent clip (51) onto the braided implant (10) by inserting an opening (52) of each subsequent clip (51) around and through a respective subsequent first pair of crosses (18) of the braided implant (10) and then through a respective subsequent second pair of crosses (18) of the braided implant (10). Method 1600 can also include step 1660 closing the clips (51), by electromagnetic radiation, along a length of each respective clip (51). Method 1600 can also include step 1670 extending the attachment pin (20) past the plurality of clips (51), repositioning the hypotube (30) onto the attachment pin (20), and pulling back on the braided implant (10) such that the hypotube (30) presses against the clips (51) thereby causing the braided implant (10) to inverted onto itself.

Figure 17B:
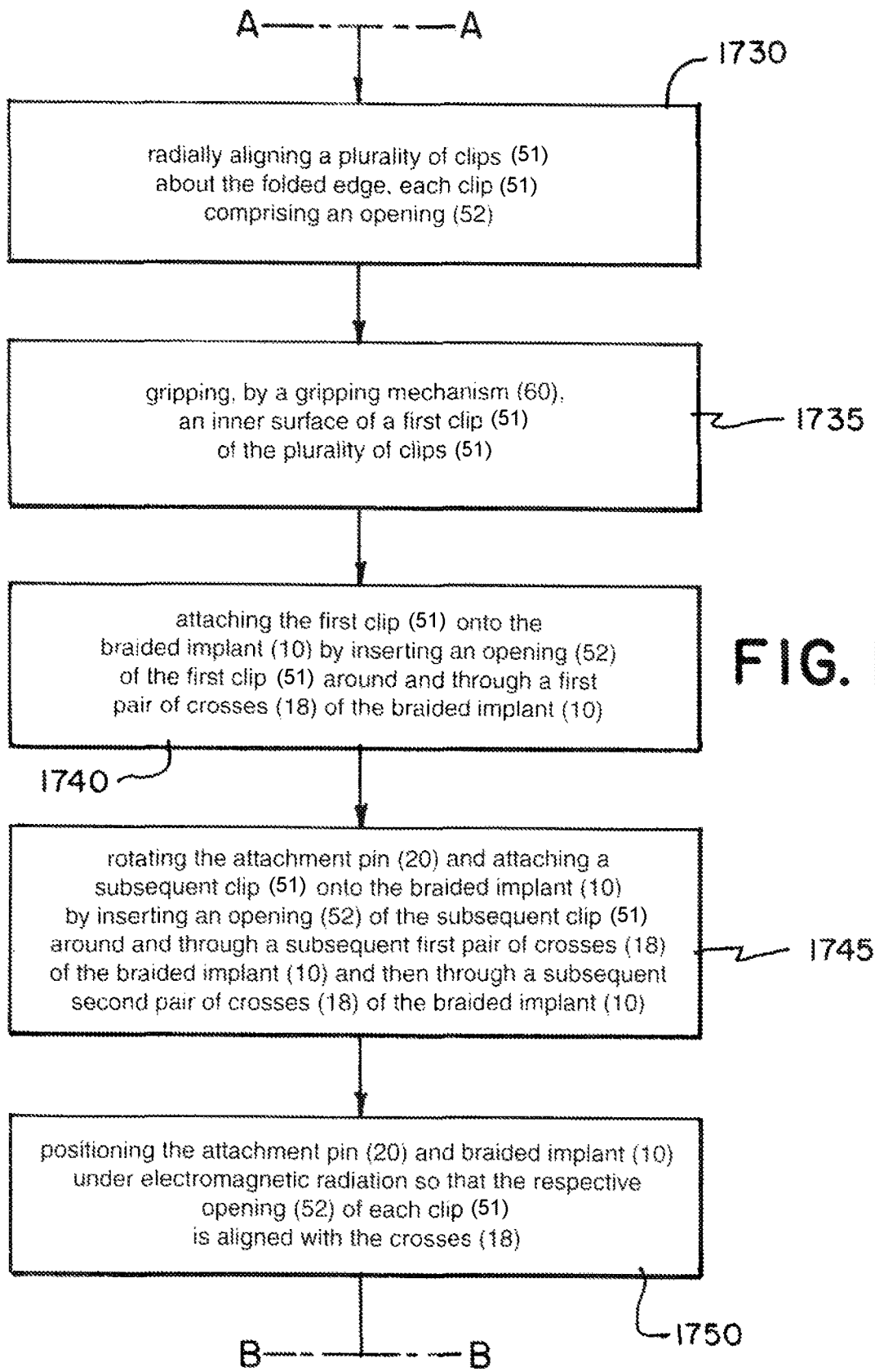
Figure 17C:
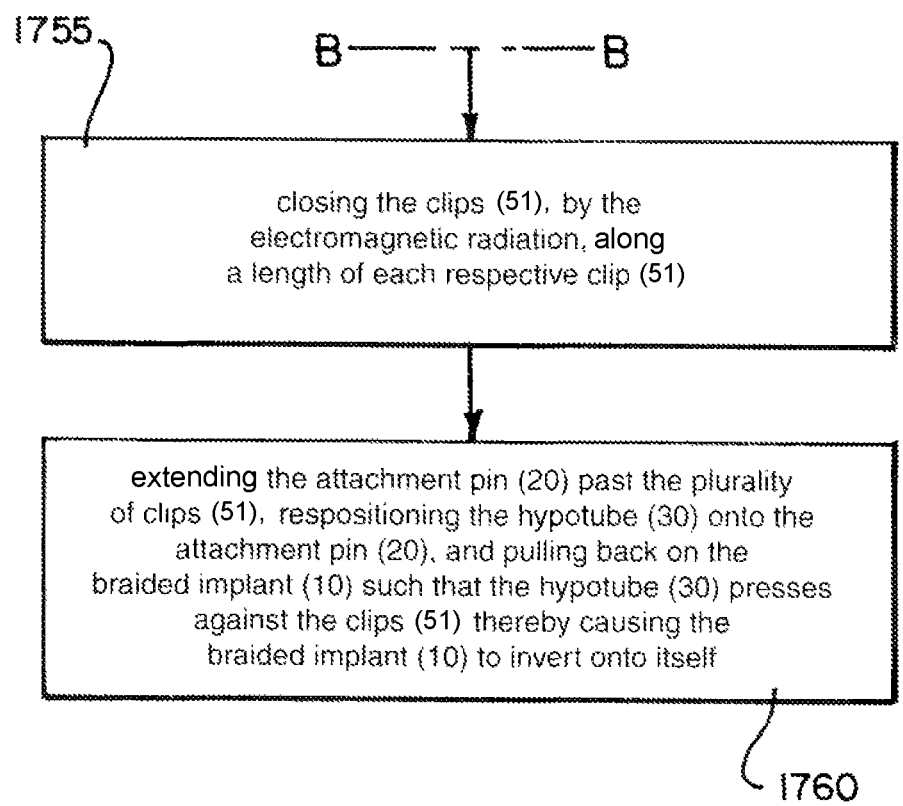

Turning to FIGS. 17a, 17b, and 17c, a schematic overview of one method 1700 of this disclosure is shown. Method 1700 can include step 1705 trimming the braided implant (10) to an initial length. Method 1700 can include step 1710 selectively positioning the braided implant (10) onto an attachment pin (20) by leaving a predetermined length (L) of the braided implant (10) extended distally from a distal end (12) of the braided implant (10) and a distal end (22) of the attachment pin (20). Method 1700 can include step 1715 distally sliding a hypotube (30) over a proximal end (14) of the braided implant (10) and onto the attachment pin (20), wherein the braided implant (10) is held in place; and the distal end (22) of the attachment pin (20) is disposed in communication with or adjacent a distal end (32) of the hypotube (30). Method 1700 can also include step 1720 inverting the braided implant (10) into itself by proximally moving the distal end (12) of the braided implant (10) over the distal end (32) of the hypotube (30). Method 1700 can include step 1725 positioning the attachment pin (20) such that the braided implant (10) is disposed vertically aligned with a microscope to view a folded edge (16) of the braided implant (10) caused by inverting the distal end (12) over the hypotube (30). Method 1700 can also include step 1730 radially aligning a plurality of clips (51) about the folded edge (16), each clip (51) comprising an opening (52).

Method 1700 can include step 1735 gripping, by a gripping mechanism (60), an inner surface of a first clip (51) of the plurality of clips (51). Method 1700 can also include step 1740 attaching the first clip (51) onto the braided implant (10) by inserting an opening (52) of the first clip (51) around and through a first pair of crosses (18) of the braided implant (10). Method 1700 can include step 1745 rotating the attachment pin (20) and attaching a subsequent clip (51) onto the braided implant (10) by inserting an opening (52) of the subsequent clip (51) around and through a subsequent first pair of crosses (18) of the braided implant (10) and then through a subsequent second pair of crosses (18) of the braided implant (10). Method 1700 can also include step 1750 positioning the attachment pin (20) and braided implant (10) under electromagnetic radiation so that the respective opening (52) of each clip (51) is aligned with the crosses (18). Method 1700 can include step 1755 closing the clips (51), by the electromagnetic radiation, along a length of each respective clip (51). Method 1700 can also include step 1760 extending the attachment pin (20) past the plurality of clips (51), repositioning the hypotube (30) onto the attachment pin (20), and pulling back on the braided implant (10) such that the hypotube (30) presses against the clips (51) thereby causing the braided implant (10) to inverted onto itself.

The descriptions contained herein are examples illustrating the various embodiments and are not intended to limit the scope of the disclosure. As described herein, the invention contemplates many variations and modifications of a system, device, or method that can be used. Variations can include but are not limited to alternative geometries of elements and components described herein, utilizing any of numerous materials for each component or element (e.g. radiopaque materials, memory shape metals, etc.), utilizing additional components including components to position or assemble the braid 10 with one or more expansion ring 50 of this disclosure. These modifications would be apparent to those having ordinary skill in the art to which this invention relates and are intended to be within the scope of the claims which follow.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method of manufacturing a braided implant for an aneurysm, the method comprising:

distally sliding a hypotube over a proximal end of the braided implant and onto an attachment pin;

inverting the braided implant into itself by proximally moving a distal end of the braided implant over a distal end of the hypotube and forming a folded edge of the braided implant;

radially aligning a plurality of clips of an expansion ring about the folded edge, each clip of the plurality of clips comprising an opening;

gripping an inner surface of a first clip of the plurality of clips and attaching the first clip onto the braided implant by inserting an opening of the first clip around and through a first pair of crosses;

rotating the attachment pin and repeating the step of attaching for each subsequent clip onto the braided implant by inserting an opening of each subsequent clip around and through a respective subsequent first pair of crosses of the braided implant and then through a respective subsequent second pair of crosses of the braided implant;

welding the clips along a length of each respective clip and an inner surface of the braided implant;

extending the attachment pin past the plurality of clips, repositioning the hypotube onto the attachment pin, and pulling back on the braided implant such that the hypotube presses against the clips thereby causing the braided implant to invert onto itself;

trimming the braided implant to an initial length;

selectively positioning the braided implant onto the attachment pin by leaving a predetermined length of the braided implant extended distally from the distal end of the braided implant and a distal end of the attachment pin, the braided implant being held in place;

positioning the distal end of the attachment pin in communication with or adjacent the distal end of the hypotube;

positioning the attachment pin such that the braided implant is disposed vertically aligned with a microscope to view the folded edge of the braided implant caused by inverting the distal end over the hypotube; and positioning the attachment pin and braided implant under electromagnetic radiation so that the respective opening of each clip is aligned with the first and second pair of crosses.

2. The method of claim 1, wherein the plurality of clips consists of four clips that form the expansion ring comprising four-leaves, the method further comprising:

rotating the attachment pin and attaching a third clip of the plurality of clips onto the braided implant by inserting an opening of the third clip around and through a first pair of crosses of the braided implant adjacent the third clip and then through a subsequent second pair of crosses of the braided implant adjacent the third clip; and rotating the attachment pin and attaching a fourth clip of the plurality of clips onto the braided implant by inserting an opening of the fourth clip around and through a first pair of crosses of the braided implant adjacent the fourth clip and then through a subsequent second pair of crosses of the braided implant adjacent the fourth clip.

3. The method of claim 1, further comprising:

repeating the steps of extending the attachment pin past the plurality of clips, repositioning the hypotube onto the attachment pin, and pulling back on the braided implant for each of the plurality of clips to complete this unit.

4. The method of claim 1, the method further comprises:

closing each of the clips by electromagnetic radiation at three separate locations located along the length of the respective clip and along an inner surface of the braided implant; and positioning the braided implant into a transport tube.

5. The method of claim 1, wherein each of the respective crosses are adjacent the respective clip to the braided implant.

6. The method of claim 1, further comprising: positioning a tip of at least one of the clips into the hypotube up to 0.5 mm.

7. The method of claim 1, further comprising: forming a symmetric pattern with each clip having a mirror image on opposite sides of the braided implant.

8. The method of claim 1, wherein the initial length is selected by determining a diameter of the braided implant; and determining the initial length appropriate for the braided implant by referring to a table of initial lengths sorted by diameter.

9. The method of claim 1, further comprising:

loading the braided implant into a fixture; and placing the fixture over the braided implant.

10. The method of claim 9, wherein the fixture includes four quadrants corresponding to openings of the clip, and wherein the step of rotating the attachment pin includes rotating the attachment pin from one quadrant to the next.

11. The method of claim 1, wherein the first pair of crosses is a double round engagement and the second pair of crosses is a double platinum.

12. The method of claim 1, wherein the first pair of crosses is a double round engagement and the second pair of crosses is a round engagement in a first location of engagement.

13. The method of claim 1, wherein the expansion ring further comprises adjoining upper and lower legs.

14. The method of claim 1, wherein each of the plurality of clips are engaged with crosses that comprise a double round pair if the clips are disposed in a predetermined quadrant location.

15. The method of claim 4, wherein the closing step comprises welding.

* * * * *